United States Patent [19]
Alvarez et al.

[11] Patent Number: 5,856,196
[45] Date of Patent: *Jan. 5, 1999

[54] PROCESSES FOR QUANTITATING PHOSPHOGLYCERIDES IN A LIPID MIXTURE AND DIAGNOSTIC USES THEREFOR

[75] Inventors: Juan G. Alvarez, Boston; Jack Ludmir, Chestnut Hill, both of Mass.

[73] Assignee: Beth Israel Hospital, Boston, Mass.

[*] Notice: The term of this patent shall not extend beyond the expiration date of Pat. No. 5,443,909.

[21] Appl. No.: 388,759

[22] Filed: Feb. 16, 1995

Related U.S. Application Data

[63] Continuation-in-part of Ser. No. 140,569, Oct. 25, 1993, Pat. No. 5,443,989.

[51] Int. Cl.$^6$ .................................................. G01N 33/92
[52] U.S. Cl. ........................ 436/71; 435/19; 436/104; 436/161; 436/174; 436/907
[58] Field of Search .................. 435/18, 19; 436/71, 436/103, 104, 161, 162, 174, 907; 210/656; 95/82–85, 88; 204/180.1, 182.8

[56] References Cited

U.S. PATENT DOCUMENTS

| | | | |
|---|---|---|---|
| 4,071,770 | 1/1978 | Shintizky et al. | 250/461.2 |
| 4,168,203 | 9/1979 | Takahashi | 435/21 |
| 4,233,032 | 11/1980 | Statland et al. | 436/63 |
| 4,257,771 | 3/1981 | Yee | 210/696 |
| 4,820,628 | 4/1989 | Weitz | 435/4 |
| 5,156,950 | 10/1992 | Akino et al. | 435/7.51 |
| 5,443,989 | 8/1995 | Alvarez et al. | 436/71 |

OTHER PUBLICATIONS

Joy D. Steinfeld, M.D. et al., "The Utility of the TDx Test in the Assessment of Fetal Lund Maturity", *Obstetrics & Gynecology* (Mar. 1992), vol. 79, No. 3, pp. 460–464.

Craig V. Towers, M.D. and Thomas J, Garite, M.D., "Evaluation of the New Amniostat–FLM Test for the Detection of Phosphatidylglycerol in Contaminated Fluids", *Am. J. Obstet. Gynecol.* (Feb. 1989), vol. 160, No. 2, pp. 298–303.

Thomas J. Garite, M.D. and et al., "A New Rapid Slide Agglutination Test for Amniotic Fluid Phosphatidylglycerol: Laboratory and Clinical Correlation", *Am. J. Obstet. Gynecol.* (Nov. 15, 1983), vol. 147, No. 6, pp. 681–686.

Joseph C. Touchstone et al., "(3–sn–Phosphatidyl)cholines (Lecithins) in Amniotic Fluid", *Clinical Chemistry* (1983), vol. 29, No. 11, pp. 1951–1954.

Alfred Lohninger et al., "Relationships Among Human Amniotic Fluid Dipalmitoyl Lecithin, Postpartum Respiratory Compliance, and Neonatal Respiratory Distress Syndrome", *Clinical Chemistry* (1983), vol. 29, No. 4, pp. 650–655.

Sylvan M. Sax et al., "Liquid–Chromatographic Estimation of Saturated Phospholipid Palmitate in Amniotic Fluid Compared with a Thin–Layer Chromatographic Method for Acetone–Precipitated Lecithin", *Clinical Chemistry* (1982), vol. 28, No. 11, pp. 2264–2268.

Michael Y. Tsai et al., "Improved Thin–Layer Chromatography of Disaturated Phosphatidylcholin in Amniotic Fluid", *Clinical Chemistry* (1981), vol. 27, No. 2, pp. 239–242.

John Torday, Ph.D. et al., "Saturated Phosphatidylcholine in Amniotic Fluid and Prediction of the Respiratory–Distress Syndrome", *The New England Journal of Medicine* (Nov. 8, 1979), vol. 301, No. 19, pp. 1013–1018.

George D. Cherayil, Ph.D. et al., "Amniotic Fluid Lecithin/Sphingolyelin Ratio Changes Related to Centrifugal Force", *Obstetrics & Gynecology* (Dec. 1977), vol. 50, No. 6, pp. 682–688.

Mikko Hallman, M.D. et al., "Phosphatidylinositol and Phsophatidylglycerol in Amniotic Fluid: Indices of Lung Maturity", *Am. J. Obstet. Gynecol.* (Jul. 1, 1976), vol. 125, No. 5, pp. 613–617.

Philip M. Farrell and Mary Ellen Avery, "Hyaline Membrane Disease", *American Review of Respiratory Disease* (1975) *American Review of Respiratory Disease*, vol. III, pp. 657–688.

Louis Gluck, M.D. et al., "The Interpretation and Significance of the Lecithin/Sphingomyelin Ratio in Amniotic Fluid", *Am. J. Obstet. Gynecol.* (Sep. 1, 1974), vol. 120, No. 1, pp. 142–155.

Donald W. Thibeault, M.D. and Calvin J. Hobel, M.D., "The Interrelationship of the Foam Stability Test, Immaturity and Intrapartum Complications in the Respiratory Distress Syndrome", *Am. J. Obstet. Gynecol.* (Jan. 1, 1974), vol. 118, No. 1, pp. 56–61.

Louis Gluck, M.D. and Marie V. Kulovich, "Lecithin/Sphingomyelin Ratios in Amniotic Fluid in Normal and Abnormal Pregnancy", *Amer. J. Obstet. Genec.* (Feb. 15, 1973); vol. 115. No. 4, pp. 539–546.

Louis Gluck, M.D. et al., "Diagnosis of the Respiratory Distress Syndrome by Amniocentesis", *Amer. J. Obstet. Gynec.* (Feb. 1, 1971), vol. 109, No. 3, pp. 440–445.

*Primary Examiner*—Jill Warden
*Assistant Examiner*—Jan M. Ludlow
*Attorney, Agent, or Firm*—LaHive & Cockfield, LLP

[57] ABSTRACT

Processes for detecting or quantitating a particular phosphoglyceride in a sample containing the phosphoglyceride and other lipids and clinical uses for the process (e.g. for diagnosing improperly functioning lungs and other conditions) are disclosed.

31 Claims, 6 Drawing Sheets

PROCESSES FOR QUANTITATING PHOSPHOGLYCERIDES IN A LIPID MIXTURE AND DIAGNOSTIC USES THEREFOR

RELATED APPLICATIONS

This application is a continuation-in-part of U.S. application Ser. No. 08/140,569, filed Oct. 25, 1993, entitled METHODS FOR ASSESSING FETAL LUNG MATURITY USING AMNIOTIC FLUID SAMPLES by Juan G. Alvarez and Jack Ludmir, now U.S. Pat. No. 5,443,989.

BACKGROUND OF THE INVENTION

A major dilemma encountered by obstetricians on a daily basis is whether to deliver a woman in preterm labor (onset of labor at $\leq 37$ weeks of gestational age), or with some underlying disease that could be alleviated by terminating the preterm pregnancy. If the baby is delivered and the baby's lungs are not mature, or are borderline, the baby will develop Respiratory Distress Syndrome (or "RDS") which can result either in fetal death or long-lasting periods of repeated respiratory difficulty. The prevalence of RDS when the gestational age is below 31 weeks is 60%, but drops to 1% by a gestation of 36 weeks. It is estimated today that in the metropolitan Boston area alone, the number of patients that need to be tested for the assessment of fetal lung maturity (or "FLM") is about 4,000 per year.

Immature fetal lungs lack an adequate surfactant layer which normally lines the alveoli and helps to keep the alveoli open after exhalation. The quantity of phospholipids generally in amniotic fluid, and of dipalmitoyl phosphatidyl choline (or "DPPC") in particular, has been correlated with the amount of surfactant lining the alveoli, and with the degree of fetal lung maturity. Phosphatidyl choline (or "PC") fractional species represent nearly 80 percent of the surfactant phospholipid varieties in the fetal lung (Clements, *Am. Rev. Resp. Dis.*, 101:984 (1970)); and dipalmitoyl phosphatidyl choline (or "DPPC") constitutes about 60 percent of the fetal lung phosphatidyl choline species fraction. Other PC fraction species include 1-palmitoyl, 2-palmitoleoyl-PC (20%); 1-palmitoyl, 2-oleoyl-PC (10%); and other minor PC varietal species (10%). The remaining lung surfactant phospholipid components also include phosphatidyl inositol, phosphatidyl ethanolamine, sphingomyelin and phosphatidyl serine. Interestingly enough, the second major phospholipid of lung surfactants is phosphatidyl glycerol, comprising more than 10 percent of the mature surfactant in the lining of the lung (Pleger and Thomas, *Arch. Intern. Med*, 127:863 (1971); Hallman and Gluck, *Biochem. Biophys. Res. Commun.* 60:1 (1974)).

A variety of assays and testing techniques have been developed and used to estimate fetal lung maturity—with markedly different degrees of success. Some of these conventional assay methods employ thin layer chromatography (or "TLC") as a requisite part of the assay. Nevertheless, despite the inclusion of TLC within these assays, and notwithstanding the improvements in the techniques of thin layer chromatography in the last decade, this chromatographic technique was viewed previously and remains seen today primarily as an ancestral technique and an undesirable mode of analysis for the medical field generally and the clinical environment in particular. This disinterest, reluctance and disfavor is intrinsically revealed within the range and diversity of publications reporting and describing the assays.

For instance, in 1971 a test for the assessment of FLM was introduced by Gluck and his associates [*Am. J. Obstet. Gynecol.* 109:440 (1971)]. This test measures the ratio of lecithin to sphingomyelin (L/S) present in amniotic fluid by thin layer chromatography (TLC). An L/S ratio value of $\geq 2$ in amniotic fluid is considered indicative of a mature fetal lung. However, the term "lecithin" has become synonymous with and representative of a range of different phosphatidyl cholines (PCs) generally; and today designates a variety of related species that differ from each other in their fatty acid residue chain lengths and/or degree of unsaturation of the fatty acids sterified to the sn-1 and sn-2 position of the glycerol moiety commonly shared among them. The particular definition of "lecithin" used can therefore vary the results of an assay. Subsequently, in 1976, Hallman et al. introduced the determination of phosphatidyl glycerol (PG) in amniotic fluid by one-dimensional TLC as another test for the assessment of FLM [Hallman et al., *Am. J. Obstet Gynecol.* 125:613 (1976)]. A few years later, Kulovich et al. introduced the analysis of phosphatidyl glycerol (PG) in amniotic fluid using two-dimensional TLC [Kulovich et al. *Am. J Obstet Gynecol.* 135:57 (1979)]. Surprisingly, since first introduced by Gluck and Hallman, TLC analysis of surfactant-associated phospholipids in amniotic fluid has become the "gold standard" for the assessment of fetal lung maturity. TLC assay methods, however, are cumbersome at best.

Another overwhelming problem with these assays is that they were unsuitable for the assessment of FLM in samples contaminated with blood, or with meconium, or for amniotic fluid samples obtained from the vaginal pool. In 1979 an alternative test was introduced by Torday et al. for the analysis of disaturated phosphatidyl choline species (or "DSPC") from amniotic fluid [*N. Engl. J. Med.* 301:1013 (1979)]. In this publication, the DSPC test was introduced as a method for the assessment of FLM in amniotic fluid samples contaminated with either blood or meconium. The cut-off value used in the Torday et al. assay of DSPC was 5 $\mu$g/mL; values above 5$\mu$g/mL were considered mature fetal lung tissues. This DSPC test is based on the method originally described by Mason et al. for the isolation of disaturated phosphatidyl choline species using osmium textroxide [*J. Lipid Res.* 17:281 (1976)]. A further adaptation of this method was also used to measure the concentration of DSPC species in rhesus-monkey amniotic fluid as a function of gestational age. It was found that the increase in amniotic fluid DSPC species correlated with lung maturity in the fetus.

A number of deficiencies and problems, however, exist in this DSPC assay method: The test measures total disaturated lecithins which includes a variety of different chemical entities in addition to DPPC, it: 1) uses low-resolution TLC; 2) requires relatively high volumes of amniotic fluid samples ($\geq 1$ mL); 3) is time-consuming (requiring 4 to 5 h to perform); and 4) requires the use of highly toxic reagents (i.e., osmium tetraoxide and carbon tetracholoride)—all of which are substantive obstacles to widespread use of the test.

The historical reluctance and disfavor shown towards assays employing thin layer chromatography also lead to a continuing interest and desire, particularly by commercial pharmaceutical companies, for less complicated assay systems and less rigorous detection techniques for assessing fetal lung maturity. Thus, by 1976, a new test for the assessment of FLM was introduced based on the analysis of membrane-bound vesicles in amniotic fluid by fluorescence polarization, as first described by Schinitzky et al. [*Br. J Obstet. Gynaecol.* 83:833 (1976)]. In this method, a fluorophore is added to the amniotic fluid test solution containing the vesicles and the fluorophore is allowed to react with the vesicular membranes. Subsequently, when excited by plane polarized light of an appropriate wavelength, the fluorophore will emit its characteristic radiation with the same polarization as the incident light—if the molecule has not rotated with the vesicular membranes. In general, however, the angle of the emitted polarization light relative to that of the exciting light depends on how far the fluorescent molecule has interacted and rotated in the time between absorption and emission. Thus, the more fluid the vesicular membrane, the greater is the degree of rotation—resulting in relatively unpolarized fluorescent light in very fluid membranes and relatively more polarized light in less fluid membranes.

The early 1980's saw the general introduction of fluorescence polarization immunoassays for therapeutic drug monitoring determinations, with nearly every major medical center obtaining an optical instrument for this purpose. An example of such an instrument is Abbott's AMX-TDx Analyzer (Abbott Laboratories, Irving, Tex.). These instruments are highly automated and are now very well established in the clinical laboratory; and the fluorophore NBD-PC has been adapted for these instruments in a commercially available method [Tait et al., *Clin. Chem.* 32:248 (1986); Foerder et al., *Clin. Chem.* 32:255 (1986)]. Although considerable controversy remains today as to the precise mechanism producing the observed results, this method yields results that correlate well with other measures of FLM; and, in a prospective study, compared favorably with the L/S ratio standards [Tait et al., *Clin. Chem.* 33:554 (1987)]. The method appears to have been quickly adopted by the medical and clinical community; and, since the test can be carried out with the AMX analyzer as a simplified, high volume, and low cost assessment of FLM, some obstetricians have been persuaded to use it as a more convenient test methodology than any of the TLC assays.

Another important test that is currently in use in hospitals across the country is the PG agglutination test which is based on the slide agglutination test of Garite et al. [*Am. J Obstet. Gynecol.* 147:681 (1983)]. The results obtained in this study are typically compared to those data obtained by analysis of the L/S ratio, or phosphatidyl glycerol determination by TLC, and by fluorescence polarization for the assessment of FLM. The sensitivity of the PG agglutination test was judged to be near 100% and yielded a determined specificity of 65%. Test sensitivity is defined as the ability to predict FLM; test specificity is defined as the ability to predict the absence of FLM. In comparison, analysis by fluorescence polarization had a sensitivity of 100% and a specificity of 60% (40% falsely immature results).

More recently, in 1989, Craig et al. introduced an ultrasensitive phosphatidyl glycerol (PG) detection kit based on the method described previously by Garite et al. [*Am. J Obstet. Gynecol.* 160:298–303 (1989)]. This assay was said to have a lower limit of detection of 0.5 $\mu$g of PG/mL in amniotic fluid for a positive test; and the analysis could be performed within 20 to 30 minutes. Note that the original test kit described earlier by Garite et al. had a lower limit of detection of 2 $\mu$g/mL for a positive test. In their report, Craig et al. applied the ultrasensitive immunoreaction kit to the analysis of amniotic fluid obtained from the vaginal pool following premature rupture of membranes—i.e., samples contaminated with blood or meconium or patients with diabetes. Despite the lower threshold of PG detection necessary for a positive result in this new ultrasensitive test, the investigators concluded that concordance rates were not significantly increased as compared to the results obtained by Garite et al. using the original kit. However, the data obtained using either of these kits should be cautiously evaluated, if the samples are contaminated with meconium or obtained from the vaginal pool due to bacterial and/or human sperm contamination which have been shown to contain significant amounts of PG. Despite these flaws, this test is commercially available as the "Amniostat-FLM" test (Irvine Scientific, Calif.).

A number of other investigators have published a variety of assays methods and techniques for assessing fetal lung maturity. These have included the following systems: measurement of surfactant lecithin in sheep amniotic fluid [Ogawa, *J Exp. Med.* 300:112 (1972)]; foam stability [Clements et al., *N. Eng. J. Med.* 286:1077 (1972)]; surface tension [Goldkrand, et al., *Am. J Obstet. Gynecol.* 128:59 (1977)]; ratio of palmitic to stearic acid [Schirar et al., *Am. Obstet. Gynecol.*, 121:653 (1975)]; surfactant apoprotein [King et al., *J Appl. Physiol.* 39:735 (1975)]; and dipalmitoyl lecithin [Ogawa, *Biol. Neonate.* 28:18 (1976)]. With the possible exception of the amniotic fluid-foam-stability test, these methods have been difficult to use routinely or are not more reliable than the L/S ratio test or the analysis of PG by TLC, which thus remain as the gold standard for the assessment of FLM.

Overall, therefore, there remains today a continuing and long-standing need for a high-resolution, accurate and reliable assay for assessing the maturity of fetal lung tissue. Moreover, recognizing the frequency with which amniotic fluid samples are contaminated with other living cells and body fluids, the assessment method should not be markedly altered or meaningfully influenced by the presence of contaminants in the sample.

SUMMARY OF THE INVENTION

In general, the invention relates to processes for detecting or quantitating a particular phosphoglyceride in a sample containing the phosphoglyceride and other lipids (including other phospholipids and phosphoglycerides). According to the process, a phosphoglyceride specific hydrolysis is performed on a sample containing the phosphoglyceride and other lipids to hydrolyze ester bonds and yield corresponding, less polar compounds from phosphoglycerides present in the sample. The resulting less polar compounds are then detected or quantitated as an indication of the presence or quantity of a corresponding phosphoglyceride in the sample.

In one aspect, the lipid containing sample is a biological fluid and a phosphoglyceride is identified or quantitated to diagnose a disease or condition in a subject. In a preferred embodiment, the lipid containing biological fluid is comprised of lung lamellar bodies. Quantitation of lung lamellar body phosphoglycerides (e.g. dipalmitoyl phosphatidyl choline (DPPC), 1-palmitoyl, 2-palmitoleoyl phosphatidyl choline and 1-palmitoyl, 2-oleoyl-phosphatidyl choline) is useful for accurately determining whether a subject's lungs are functioning properly. For example, assessment of lung lamellar body phosphoglycerides in fetal fluids (e.g. amniotic fluid or maternal cervical secretions) is useful for preventing the birth of infants having Respiratory Distress Syndrome (RDS), by facilitating informed decision making on whether a fetus' lungs are mature enough for survival outside the womb. Alternatively, assesment of lung lamellar body phosphoglycerides in a biological fluid such as lung lavage, plasma, spinal fluid, or urine is useful for diagnosing improperly functioning lungs in an adult, due for example to adult respiratory distress syndrome (ARDS), emphysema or lung cancer. In another embodiment, the lipid containing biological fluid is comprised of bilirubin. Quantitation of a bilirubin phosphoglyceride is useful, for example, for accurately diagnosing jaundice.

Preferably a phosphoglyceride specific hydrolysis is accomplished by contacting a lipid containing sample with a phospholipase enzyme at an appropriate temperature and for an appropriate period of time for complete hydrolysis of phosphoglycerides present in the sample. Phospholipase Cs, which generate diacylglycerols (phosphoglycerols) from corresponding phosphoglycerides, especially enzymes obtained from *Bacillus cereus* or *Clostridium perfinges*, are particularly preferred for use in the disclosed process. Other phospholipases, which can accomplish phosphoglyceride specific hydrolysis and therefor are useful in the disclosed process include: phospholipase D, phospholipase $A_1$, and phospholipase $A_2$.

In addition, for accurate detection of less polar compounds generated via phosphoglyceride hydrolysis, the less polar compounds are preferably isolated from each other and from other sample components prior to or concurrent with detection. A preferred means for separating or removing the less polar compounds from other sample components is by extraction using an organic solvent. Preferable organic solvents include: chloroform-methanol, ethyl acetate, hexane-isopropanol and hexane. Separation of less polar compounds generated by phosphoglyceride specific hydrolysis from one another is preferably accomplished by a high resolution chromatography or electrophoresis. The organic solvent used for extraction can be the same as or different from the solvent used as the mobile phase of a chromatographic separation. Preferable chromatographic means, which can be performed using conventionally known techniques and commercially available equipment include liquid, column chromatographies (e.g. high performance liquid chromatography (HPLC), ion exchange chromatography, and gel chromatography); gas column chromatography (GC); and planar, liquid chromatographies (e.g. thin layer chromatography (TLC) and high performance TLC (HPTLC)). Once separated out, less polar compounds generated by phosphoglyceride specific hydrolysis can be detected visually or aided by an instrument appropriate for the separation means (e.g. spectrophotometer).

Alternatively, less polar compounds generated by phosphoglyceride specific hydrolysis can be immunologically separated from the sample (i.e. using a labelled antibody specific for the less polar compound corresponding to the phosphoglyceride to be detected) and detected by a means appropriate for detecting the label.

The newly disclosed general processes for detecting or quantitating phosphoglycerides present in a lipid containing sample offer a number of features and advantages, including: 1) requiring only a small volume of sample (e.g. 25–100 $\mu$L); 2) yielding highly reproducible results in a short period of time (within about 30 minutes); 3) being amenable to automation for analysis of multiple samples at one time; 4) being amenable to performance on previously frozen samples and 5) being safe (as no toxic chemicals are employed).

In contrast to lecithin-based fetal lung maturity (FLM) detection methods, use of the instant process to quantitate lung phosphoglycerides and thereby assess the maturity of a fetus' lungs can provide informative results using samples, which have been contaminated with blood, meconium, creatinine, human spermatozoa, vaginal secretions, and vaginal mucosa cells. In addition, informative results can be obtained using samples from a diabetic mother. Further, due to the high sensitivity (i.e. ability to predict FLM) and particularly the high specificity (i.e. ability to predict the absence of FLM) of the disclosed process for assessing FLM (estimated at about 100% and 95%, respectively) relative to prior tests, widespread use of the disclosed process will result in fewer newborns with RDS; and fewer newborns being misdiagnosed as having RDS (and therefore being inappropriately held in a hospital presumably to allow their lungs to mature). Wide-spread clinical use of the instant process for assessing FLM should therefore result in decreased medical costs.

DETAILED DESCRIPTION OF THE INVENTION

The level of phospholipids in amniotic fluid, and in particular, of dipalmitoyl phosphatidyl choline (DPPC), has been shown to correlate with the level of surfactant lining the alveoli and with fetal lung maturity (FLM). The present invention is based on the finding that a particular phosphoglyceride, such as DPPC, can be detected and accurately quantitated in the presence of other lipids including other phospholipids and phosphoglycerides, which may be present in a sample. The disclosed process involves an initial step of specifically removing the polar head group from phosphoglycerides (but not other phospholipids) present in a sample. The resulting less polar compounds can then be individually detected or quantitated using appropriate means. The disclosed processes are particularly useful for diagnosing lung conditions that result in an inappropriate level of the phosphoglyceride diphosphatidylcholine (DPPC), as well as other phosphatidyl cholines (e.g. 1-palmitoyl, 2-palmitoleoyl-phosphatidyl choline; and 1-palmitoyl, 2-oleoyl-phosphatidyl choline) present in a biological sample (e.g. amniotic fluid, lung lavage, blood plasma, cervical smear, urine or spinal fluid). "Phosphoglycerides" or "glycerol phosphatides" are phosphorus-containing lipids, "phospholipids", having the general structure shown in Table 1.

TABLE 1

General Structure of Phosphoglycerides

Wherein $R_1$ typically is a saturated fatty acid residue, and $R_2$ typically is an unsaturated fatty acid residue.

A phosphoglyceride is a phosphoric ester of glycerol, in which one or both hydroxyl groups is esterified with a saturated or unsaturated fatty acid. In addition, all phosphoglycerides contain a polar head group, namely an alcohol designated generally as "X—OH" and whose hydroxyl group is esterified directly to the phosphoric acid moiety of the structure. Since phosphoglycerides possess a polar head moiety in addition to a non-polar tail group, these compounds are amphipathic.

Phosphoglycerides can vary in size, shape, and electric charge. Each type of phosphoglyceride can exist as many different chemical species and structural forms—differing primarily in their fatty acid residue substituents and in their non-polar tail groups. Typically, one fatty acid residue (designated "$R_1$") is saturated and the other (designated "$R_2$") is unsaturated (Biochemistry, 2nd Ed., Lehninger, A. L. ed., Worth Publishers, Inc., 1975, pp. 287–295).

The process of the invention requires specific cleavage of the polar head group from the phosphoglyceride tail group, while leaving other phospholipids that may be present in the sample intact. Such a highly specific cleavage can be accomplished enzymatically, for example, by reacting the sample with a phospholipase enzyme. Phospholipases are highly specific for phosphoglycerides, but have negligible hydrolytic activity towards phosphatidyl ethanolamine, phosphatidyl serine, phosphatidyl inositol and phosphatidyl glycerol (Moreau, et al., Biochemistry 27: 2319 (1980)).

Examples of appropriate phospholipase enzymes for use in the method of the invention are listed below in Table 2:

TABLE 2

| Phospholipases* |
| --- |
| phospholipase C |
| phospholipase D |
| phospholipase $A_1$ |
| phospholipase $A_2$ |

*Source: Dixon, M. and E. Webb, Enzymes, Academic Press, 1979.

Phospholipase C hydrolyzes the phosphoester bond linking the primary hydroxyl group at the sn-3 position of glycerol to the phosphate group to yield phosphocholine and a diacylglycerol. Phospholipase D, on the other hand, hydrolyzes the phosphoester bond that links the choline base to the phosphate group to yield choline and phosphatidic acid. Phospholipase $A_1$ hydrolyzes the ester bond (i.e. the bond formed from a dehydrolysis reaction between an acid (R—COOH) and a base (R—OH)) at the sn-1 position of glycerol to yield free fatty acid and 1—OH-2-acyl-phosphorylcholine (1-lysophosphatidylcholine). And phospholipase $A_2$ hydrolyzes the ester bond at the sn-2 position of the glycerol to yield 1-acyl-2—OH-phosphocholine (2-lysophosphatidylcholine).

Phospholipase enzymes obtained from various bacterial species are available commercially. Phospholipase C, particularly the type obtained from *Bacillus cereus* or *Clostridium perfinges* are preferred for performing the hydrolysis reaction required by the disclosed method. Different phospholipase enzymes may require slightly different temperatures and time periods to effect hydrolysis. *Bacillus cereus* and *Clostridium perfinges* perform optimal hydrolysis of phosphoglycerides in about 5 minutes at about 37° C. (See FIG. 3).

The less polar compounds generated by phosphoglyceride specific hydrolysis (e.g. diacylglycerols, phosphatidic acids, 1-lysophosphatidylcholines, and 2-lysophosphatidylcholines) can then be detected. Preferably these less polar compounds are isolated from other components of the biological sample prior to detection and/or quantitation. For example, the less polar compounds can be extracted from the sample using an organic solvent and then resolved from one another (e.g. via chromatography or electrophoresis). Examples of organic solvents used for extraction include: chloroform- methanol, ethyl acetate, hexane-isopropanol and hexane.

An organic solvent used for extraction can be the same as or different from the solvent subsequently used as the mobile phase of a liquid chromatographic separation either by a column (e.g. high performance liquid chromatography (HPLC), ion exchange chromatography, or gel chromatography) or a planar, liquid chromatography (e.g. thin layer chromatography (TLC) or high performance TLC (HPTLC)). The mobile phase should be a gas, such as hexane when performing gas chromatography.

Suitable mobile phases comprise two different but compatible organic solvent combinations. One of the solvents should be strong ($\epsilon°$ is high); and the other weak ($\epsilon°$ is low). A suitable value of the capacity factor, k' is then obtained by varying the volume ratio of the two. In HPTLC, k' is calculated according to the equation below, where Rf is the retardation factor or ratio of the distance migrated by the solute versus the solvent front:

$$k' = (1-RF)/Rf.$$

The eluent strength $\epsilon°$—which is the adsorption energy per unit area of solvent—can serve as a rough guide to the strengths of solvents for adsorption chromatography. This parameter depends upon the adsorbent with $\epsilon°$ values for silica gel being about 0.8. It has been found that an increase in $\epsilon°$ value by 0.05 unit usually decreases all k' values by a factor of 3 or 4. Thus, enormous variations in k' are possible; and at least one binary system involving the solvents in Table 3 can be found that will give adequate Rf values for nearly any sample. When overlapping peaks are encountered, exchanging one strong solvent for another while holding k' constant will provide the desired solution.

TABLE 3

Eluent Strength of Common Chromatographic Mobile Phases

| Solvent | $\epsilon°$ |
| --- | --- |
| Hexane | 0.008 |
| Toluene | 0.230 |
| Diethyl ether | 0.300 |
| Chloroform | 0.320 |
| Acetone | 0.400 |
| Ethanol | 0.700 |
| Methanol | 0.760 |
| Water | 1.880 |

Since the compounds generated by phosphoglyceride specific hydrolysis are relatively non-polar, a solvent of a low polarity like chloroform, with high affinity for hydrophobic moieties, is preferably chosen. On the other hand, since some of the generated compounds may possess some degree of polarity, ethyl acetate, acetone, dioxane and diethyl ether may be added individually or in combination with chloroform, to achieve separation of the various compounds (e.g. phospholipase C generated diacylglycerols—including dimyristoyl glycerol, dilauryl glycerol, dipalmitoyl glycerol and 1-palmitoyl, 2-oleoylglycerol).

The solvent combination chloroform-ethyl acetate (90:10, v/v) was initially tried for the separation of the various diacylglycerols. Chloroform has an $\epsilon°$ of 0.40, and ethyl acetate an $\epsilon°$ of 0.58. Since no separation of the diacylglycerol standard mixture was achieved using this solvent mixture as the mobile phase, the volume ratios were changed to 85:15, 90:10, and 95:5—also with no success. Therefore, ethyl acetate was exchanged for another solvent of similar $\epsilon°$, such as acetone. Various volume ratios of chloroform-acetone were used as solvent mixtures. These included chloroform-acetone ratios of: 80:20, 85:15, 90:10, 91:9, 92:8, 93:7; 94:6; 95:5.5; 95:5, 96:4; 97:3; and 98:2. A volume ratio of chloroform-methanol 95:5.5 was found to give optimal resolution of the various diacylglycerols tested. When used as the mobile phase, this solvent mixture provides resolution of the various less polar species generated by phosphoglyceride specific hydrolysis and minimizes comigration with other non-polar lipid components including triglycerides and cholesterol.

For obtaining optimal resolution using HPTLC, preferably the high performance silica gel layers are cationically mass modified (e.g. using silver nitrate ($AgNO_3$) in a process known as argentation; or using boric acid ($BH_4$)). Cationic interactions in the silica gel stationary phase with the $\pi$ orbitals of the fatty acid double bond(s) during separation allows resolution of the less polar compounds released from phosphoglycerides in which at least one of the fatty acids esterified to the glycerol moiety has one double bond. Another net effect of the use of mass modified high performance layers combined to the use of low polarity index solvents—i.e., chloroform and acetone—is that those species containing longer aliphatic chains migrate faster than those with shorter ones. This results, for example, in the migration of dipalmitoyl glycerol faster than dimyristolylglycerol but slower than di-stearoylglycerol. Cationically modified silica gels, however, preclude use of more polar solvents in the mobile phase (e.g. methanol and water, See Table 3).

Once separated out, less polar compounds generated by phosphoglyceride specific hydrolysis can be detected visually or aided by an instrument appropriate for the separation means (e.g. optical, near infrared or infrared spectrophotometer; or reflectance densitometer).

An alternate methodology for detecting or quantitating a phosphoglyceride relies on the high affinity and specificity of antibodies. Specific antibodies (e.g. polyclonal or monoclonal) against a particular phosphoglyceride or a less polar compound generated by phosphoglyceride specific hydrolysis of a phosphoglyceride may be produced and appropriately labeled ( e.g. with peroxidase, fluorophore, radioactive isotope or latex particle) using standard immunological and immunochemical procedures. An optical instrument, such as Abbott's AMX-TDx Analyzer (Abbott Laboratories, Irving, Tex.), which is well established in the clinical laboratory, can be used to detect or quantitate antibody bound phosphoglyceride or hydrolyzed products of phosphoglycerides, where the label is fluorescent.

Because healthy, mature lungs have phosphoglyceride containing lamellar bodies, the condition of a subject's lungs can be assessed using the general methodology described above. For example, assesment of lung lamellar body phosphoglycerides (e.g. dipalmitoyl phosphatidyl choline (DPPC), 1-palmitoyl, 2-palmitoleoyl phosphatidyl choline and 1-palmitoyl, 2-oleoyl-phosphatidyl choline) in a biological fluid such as lung lavage, plasma, spinal fluid, or urine is useful for diagnosing improperly functioning lungs in an adult, due for example to adult respiratory distress syndrome (ARDS), emphysema or lung cancer. Alternatively, assessment of lung lamellar body phosphoglycerides in fetal fluids (e.g. amniotic fluid or maternal cervical secretions) is useful for preventing the birth of infants having Respiratory Distress Syndrome (RDS), by facilitating informed decision making on whether a fetus' lungs are mature enough for survival outside the womb.

The following lung surfactant phospholipids have been found to be present in an amount equal to about the following indicated percentage of total lipids in amniotic fluid: 1) phosphatidyl choline (lecithin), "PC": 80–85%; 2) dipalmitoyl phosphatidyl choline (lecithin), "DPPC": 45–50%; 3) 1-palmitoyl phosphatidyl choline, "IPPC": 85%; 4) 2-palmitoyl phosphatidyl choline, "2PPC": 46%; 5) 1-palmitoyl, 2-oleoyl phosphatidyl choline, "POPC": 8%; 6) phosphatidyl ethanolamine (cephaline), "PEA": 3–5%; 7) phosphatidyl inositol, "PI": 2%; 8) phosphatidyl serine, "PS": 1%; and phosphatidyl glycerol, "PG": 6–11%. Of the different phosphoglycerides present in amniotic fluid, dipalmitoyl phosphatidyl choline (DPPC) has been found to be the most representative quantitatively of the degree of maturity in fetal lung tissue.

As described in detail in the following Example 1, DPPC and POPC standards hydrolyzed with phospholipase C and analyzed by AgNO$_3$-modified high-performance thin-layer chromatography (HPTLC)-reflectance densitometry, resulted in bands that comigrated with dipalmitoyl glycerol and palmitoyl-palmitoleoyl glycerol, respectively, and with the components released following enzymatic hydrolysis of amniotic fluid.

The identity of these components was further established by gas chromatographic analysis of the fatty acid methyl esters released following alkaline methanolysis. Gas chromatographic analysis of the fatty acid methyl esters released after alkaline methanolysis of the component comigrating with dipalmitoyl glycerol resulted in a single peak that had the same retention time as methyl hexadecanoate (16:0). Similarly, gas chromatographic analysis of the fatty acid methyl esters released following alkaline methanolysis of the component comigrating with palmitoyl-palmitoeloyl glycerol resulted in two peaks of equal intensity (1:1 peak ratio) that had the same retention time as methyl hexadecanoate (16:0) and methyl hexadecenoate (16:1), respectively. This data is consistent with the phospholipid composition of mature fetal lung surfactant obtained from amniotic fluid where the major components are the DPPC and POPC molecular species.

Figure 1:
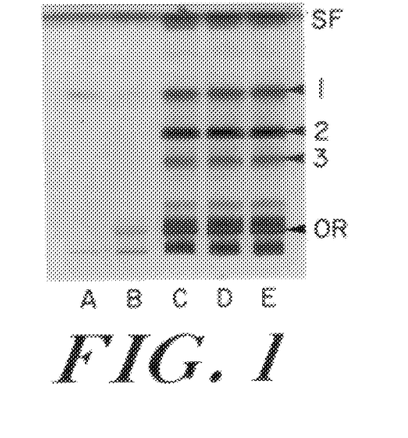
FIG. 1: Chromatogram of amniotic fluid lipids following enzymatic hydrolysis with phospholipase C. Lane A corresponds to 0.24 $\mu$g of dipalmitoylglycerol standard; lane B corresponds to phospholipase C blank; and lanes C, D, and E correspond to triplicate 25 $\mu$L aliquots of term amniotic fluid treated with phospholipase C; 1: dipalmitoyl glycerol; 2: cholesterol; 3: palmitoyl-palmitoleoyl glycerol. SF: solvent front; OR: origin.
Figure 2:
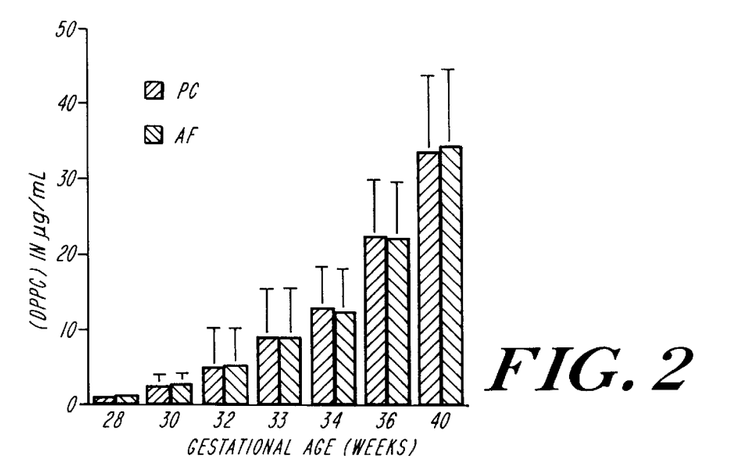
FIG. 2: Levels of DPPC in amniotic fluid as a function of gestational age. PC: phosphatidyl choline extracted from amniotic fluid was hydrolyzed with phospholipase C and the resulting DPG analyzed by HPTLC (see materials and methods); AF: amniotic fluid was hydrolyzed with phospholipase C and the resulting DPG analyzed by micro-HPTLC. Each point represent the average of 5 separate experiments. Error bars are the standard deviations.

In order to ascertain that phosphatidyl choline was the sole phospholipid source of the component comigrating with DPG following enzymatic hydrolysis with phospholipase C, phosphatidyl choline was isolated from amniotic fluids obtained by amniocentesis at gestational ages ranging from 28 to 40 weeks. The purified phosphatidyl choline was then hydrolyzed with phospholipase C and the resulting diacylglycerols analyzed by micro-HPTLC, as indicated previously. As shown in FIG. 1, DPG values obtained following phospholipase C hydrolysis of amniotic fluid and/or phosphatidyl choline isolated from the same amniotic fluid, increased with gestational age. The concentration of POG increased sharply with DPG concentrations above 1,200 µg/100 mL. The differences in the DPG values for both set of samples were not statistically significant (p>0.5). Therefore, analysis of DPG by HPTLC reflectance spectrodensitometry following enzymatic hydrolysis of amniotic fluid with phospholipase C can be safely utilized to determine the concentration of DPPC in that amniotic fluid.

Figure 3:
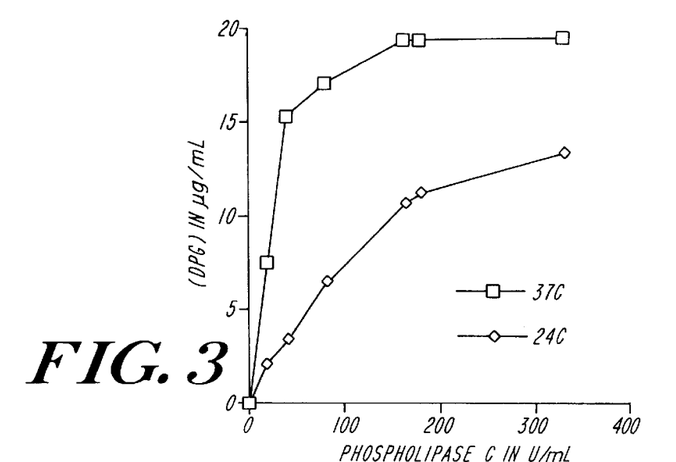
FIG. 3: Dependency of rate of hydrolysis of amniotic fluid with phospholipase C on enzyme concentration and temperature. Each point represents the average of separate experiments at the various phospholipase C concentration selected. Hydrolysis time was 5 min.
Figure 4:
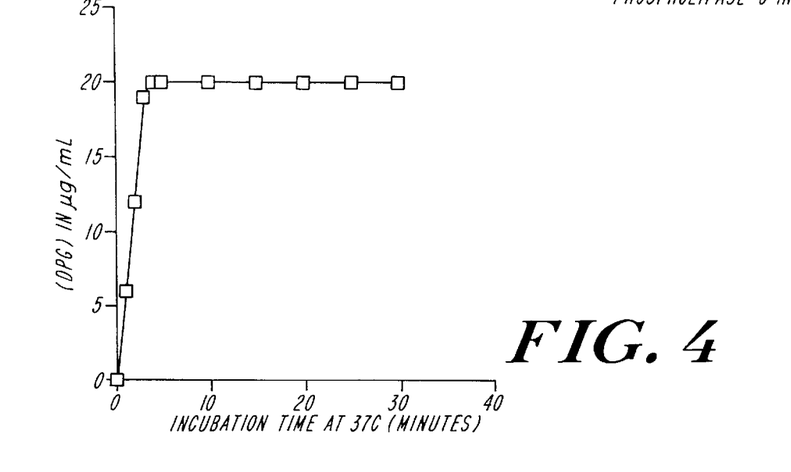
FIG. 4: Time dependency of amniotic fluid hydrolysis with phospholipase C. Each point represents the mean of 5 separate experiments at the time points selected.
Figure 5:
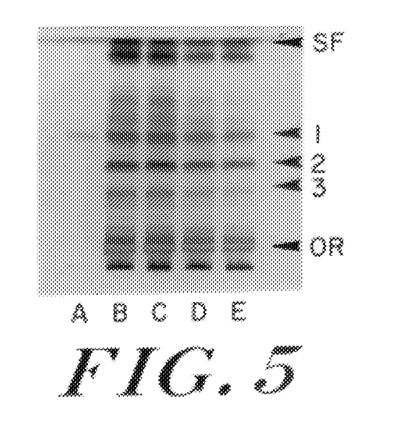
FIG. 5: Effect of centrifugation on the concentration of DPPC in Amniotic Fluid. Lane A corresponds to 0.24 $\mu$g of dipalmitoylglycerol standard; lanes B and C correspond to 25$\mu$L aliquots of an uncentrifuged blood and meconium contaminated term amniotic fluid sample; lanes D and E correspond to the same amniotic fluid sample centrifuged at 1,000 g for 10 min; 1: dipalmitoyl glycerol; 2: cholesterol; and 3: palmitoylpalmitoleoylglycerol. SF: solvent front; OR: origin.

The rate of hydrolysis of DPPC was temperature, phospholipase C concentration, and time dependent. As shown in FIGS. 3 and 4, optimal hydrolysis was obtained at a phospholipase C concentration of 160 U/mL at 37° C. for 5 min. The rate of hydrolysis of POPC was also temperature, phospholipase C concentration, and time dependent. Treatment of amniotic fluid with phospholipase C did not result in any significant hydrolysis of phospholipids other than phosphatidylcholine. Addition of up to 10% of blood, meconium did not result in any significant change in the rate of hydrolysis (p>0.7). The effect of blood and meconium contamination on the resolution of DPG and POG from other lipids is illustrated in FIG. 5. The effect of centrifugation on the concentration of DPPC and POPC, is also shown in FIG. 5. Lanes B, C, D and E of FIG. 5 correspond to a term amniotic fluid sample before and after centrifugation at 3,000 g for 10 minutes. Centrifugation at this speed resulted in a net loss of 40 to 50%±10.5 of the of DPPC present in the uncentrifuged samples. Increasing the centrifugation speed to 14,000 g resulted in a net DPPC loss of 90%. No significant differences were found in the values of DPPC obtained with the fresh samples compared to those obtained with the frozen specimens subjected to three cycles of freeze/thaw.

The efficiency of DPPC hydrolysis and extraction was determined by spiking amniotic fluid samples with known amounts of [$^{14}$C]-DPPC and measuring the concentration of [$^{14}$C]-DPG in the lower phase. The recoveries obtained ranged between 91% and 98% as determined by HPTLC-autorradiographic analysis.

Figure 6:
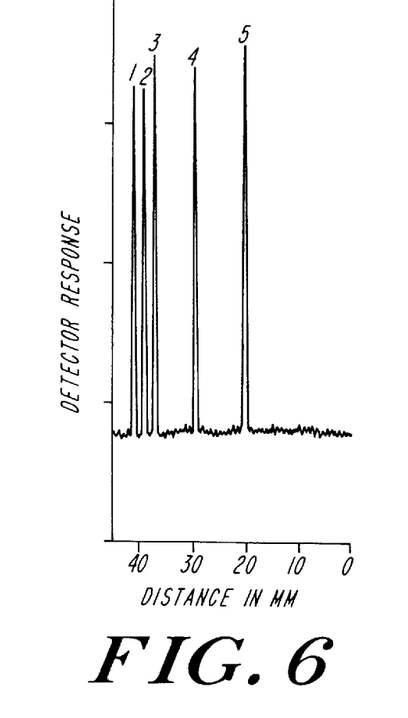
FIG. 6: Densitometric chromatogram of disaturated and monounsaturated diacylglycerols standards separated by HPTLC. 1: distearoylglycerol; 2: dipalmitoylglycerol; 3: myristolpalmitoylglycerol; 4: dimyristoylglycerol; and 5: palmitoylpalmitoleoyl glycerol. Aliquots of 0.1 $\mu$g of each standard were applied to separate lanes and resolved by micro-HPTLC.

The separation of DPG from other diacylglycerol species is shown in FIG. 6. DPG was resolved from dimyristoylglycerol, distearoylglycerol, myristoylpalmitoylglycerol, palmitoyl palmitoleoyl glycerol, palmitoyloleoylglycerol, and free cholesterol. Gas chromatographic analysis of the fatty acid methyl esters released following alkaline hydrolysis of phosphatidyl choline isolated from amniotic fluid indicated that methyl tetradecanoate (14:0), methyl hexadecanoate (16:0), methyl hexadecenoate (16:1), methyl octadecanoate (18:0), and methyl octadecenoate (18:1) comprised 2%, 86%, 5%, 3%, and 4% of the total fatty acid content, respectively. Based on this fatty acid profile, should other 1,2-disaturated diglyceride species different from that of the diglyceride standards used in this study comigrate with DPG, their contribution to the DPG value obtained will be $\leq$3%.

The lower limit of detection of DPPC in amniotic fluid as analyzed by the method described was 200 ng/mL with linear detector response extended to 30 µg/mL. The intra- and inter-assay variation for analysis of DPPC as measured by the standard deviation were 3 and 8%, respectively. The turn-around analysis time for triplicate aliquots of amniotic fluid was 40 min.

Based on a number of experiments performed on a number of different amniotic fluid samples, it was determined that for a normal pregnant women, a value of less than about 12 µg DPG/mL amniotic fluid is indicative of an immature fetal lung, and a value of greater than or equal to about 12 µg DPG/mL amniotic fluid is indicative of a mature fetal lung; and for a diabetic pregnant woman, a value of less than about 14 µg DPG/mL amniotic fluid is indicative of an immature fetal lung, a value of greater than or equal to about 16 µg DPG/mL amniotic fluid is indicative of a mature fetal lung.

As compared to the method reported by Torday et al. (Torday et al. (1979) *N. Engl J Med,* 301:1013) for the determination of disaturated phosphatidyl choline (DSPC) in amniotic fluid, analysis of DPPC by the method described herein offers the following advantages: 1) it minimizes sample use: only 25 µL of amniotic fluid are required for analysis.; 2) it provides a fast turn-around time, allowing analysis of triplicate aliquots of amniotic fluid in 40 min; 3) it minimizes the use of toxic reagents, i.e., osmium tetraoxide and carbon tetrachloride; 4) it measures DPPC, the most abundant component of the mature lung surfactant; 5) it provides quantitative analysis of other key components of fetal lung surfactant including POPC; and 6) it can also be applied to the analysis of frozen specimens of amniotic fluid. The main disadvantage of this method as of any other method that provides quantitative analysis of a single component in a biological fluid, including the DSPC method, is that the value obtained is subjected to volume fluctuations. Therefore, in those situations where the volume of amniotic fluid is below the normal level (oligohydramnios) the concentration of DPPC in amniotic fluid will be artificially increased. And conversely, when the volume is higher than normal (polihydramnios), the concentration will be decreased. Adjustment of the values obtained can be made in these infrequent situations.

In addition to being useful for diagnosing the condition of a subject's lungs, the disclosed methodologies are useful for detecting or quantitating other phosphoglycerides, the level of which is indicative of certain diseases or conditions. For example, certain phosphoglycerides comprise bilirubin. In a normal subject, serum bilirubin generally ranges from about 0.5 to 1.0 mg/dL. However, when a subject is jaundiced, the levels exceed 2.5 mg/dL. Detection or quantitation of certain phosphoglycerides in a biological fluid obtained from a subject according to the disclosed processes, can provide a rapid and accurate means to diagnose jaundice and other conditions associated with the bilirubin level of a subject.

The present invention is further illustrated by the following examples which should not be construed as limiting in any way. The contents of all cited references (including literature references, issued patents, published patent applications, and co-pending patent applications) cited in the Examples and throughout this application are hereby expressly incorporated by reference.

EXAMPLE 1

Analyzing Amniotic Fluid for Lamellar Body Phosphoglycerides as an Indication of Fetal Lung Maturity Reagents and Materials The lipid standards including dipalmitoyl phosphatidylcholine, palmitoylpalmitoleoyl phosphatidyl choline, dipalmitoylglycerol, palmitoylstearoylglycerol, dimyristoylglycerol, distearoylglycerol, palmitoylpalmitoleoylglycerol, palmitoyloleoylglycerol, all 1,2-diglycerides; free cholesterol, *Bacillus cereus* phospholipase C (Sigma Type XI, 1,000U/0.6 mL), and Kodak X-Omat film, were purchased from Sigma Chemical Co (St. Louis, Mo.). L-3-phosphatidyl choline, 1,2-di-[-1-$^{14}$C]-palmitoyl (100–120 mCi/mmol) ([$^{14}$C]-DPPC) was obtained from Amersham Corporation (Arlington Heights, Ill.). Dulbecco's phosphate-buffered saline (D-PBS) was obtained from Gibco-Life Technologies Inc. (Grand Island, N.Y.). Kimble disposable centrifuge tubes were obtained from Thomas Scientific. Precoated silica gel HP-K high-performance microplates (5×5 cm, 250 μm thickness) were obtained from Whatman (Clifton, N.J.). Solvents were EM Science chromatographic grade. Inorganic salts were from J. T. Baker (Phillisburg, N.J.) and of the highest purity available.

Methods

Hydrolysis with *Bacillus cereus* Phospholipase C

Amniotic fluid samples obtained by amniocentesis for cytogenetic analysis (15 to 18 weeks gestational age) were spiked with dipalmitoyl phosphatidyl choline standard to obtain concentrations ranging between 0.2 and 30 μg/mL. Aliquots of 0.5mL of amniotic fluid were then hydrolyzed with Bacillus Cereus phospholipase C at concentrations that ranged between 20 and 300 U/mL, and incubated at 24° C. and 37°° C. for up to 30 min. Aliquots of 25 μl were then removed at 5 min intervals for the various phospholipase C concentrations and temperatures selected and the resulting diacylglycerols analyzed as indicated below. Solutions of phospholipase C in D-PBS were stored at 4° C. and were stable for up to 1 month.

Specificity of Hydrolysis of Phosphatidylcholines by *Bacillus cereus* Phospholipase C The effect of amniotic fluid hydrolysis with *Bacillus cereus* phospholipase C on the concentration of phospholipids other than phosphatidylcholine, was also tested. Aliquots of 25 μL of amniotic fluid were added to 10 mL centrifuge glass conical tubes, and treated with either 25 μL of *Bacillus cereus* phospholipase C (160 U/mL) or 25 μL of D-PBS. The samples were then incubated at 37° C. for 5 min, 0.3 mL of C-M (2: 1, v/v) added, the emulsion separated at 600 g for 3 min, the lower phase aspirated and evaporated to dryness, and the lipid residue dissolved in 4 μL of C-M (1:1, v/v). Aliquots of 4 μL were applied to Whatman HP-K silica gel plates, the plates predeveloped in C-M (1:1, v/v) to 1 cm, and developed in one dimension using chloroform-ethanol-triethylamine-water (30:34:30:8, v/v/v/v) as the mobile phase. Following development, the plates were dipped for 5s in a 10% solution of $CuSO_4$ in 8% $H_3PO_4$ and placed on a CAMAG TLC Plate Heater III at 175° C. for 8 min. The stained chromatograms were then scanned with a Shimadzu CS-9000 spectrodensitometer in the reflectance mode at 400 nm [J. G. Alvarez and J. Ludmir (1993) *J Chromatogr* 615: 142]. The values obtained for the various phospholipids present in the amniotic fluid samples, including phosphatidyl glycerol, phosphatidyl ethanolamine, phosphatidyl serine, phosphatidyl inositol, phosphatidyl choline, and sphingomyelin, were then compared to the untreated samples.

High-Performance Thin-Layer Chromatography

Aliquots of 25 μL of a *Bacillus cereus* phospholipase C solution (160 U/mL) in D-PBS were added to 25 μL aliquots of amniotic fluid, the reaction allowed to proceed to completion for 5 min at 37° C. and the lipids extracted by liquid-liquid partition with 0.3 mL of a mixture of chloroform-methanol (C-M) (2:1, v/v) (final C-M-AF ratio of 4:2:1, v/v/v). The resulting emulsion was separated in two phases by centrifugation at 600 g for 3 min, the lower phase aspirated, evaporated to dryness, and the lipid residue dissolved in 4 μL of C-M (1:1, v/v). Aliquots of 4 μL of the lipid extract were applied to $AgNO_3$-modified high-performance (HPTLC) Whatman 5×5 cm HP-K silica gel microplates ($AgNO_3$-modified layers were prepared by dipping HP-K microplates in a saturated solution of $AgNO_3$ in methanol for 1 minute and dried under a warm stream of air from a hair dryer for 10s), predeveloped in C-M (1:1, v/v), the plates dried, and developed in one dimension using chloroform-acetone (95:5.5, v/v) as the mobile phase. Aliquots of 4 μL of dipalmitoyl glycerol standard at a concentration of 0.06 mg/mL, were applied to a separate lane for identification and quantification purposes. A blank consisting of 25 μL of phospholipase C and 25 μL of D-PBS and a control consisting of 25 μL of D-PBS and 25 μL of amniotic fluid, were also carried through the entire procedure. Following development, the plates were dipped for 5s in a 10% solution of $CuSO_4$ in 8% $H_3PO_4$, allowed to drip in the vertical position for 30s, and placed on a CAMAG TLC Plate Heater III at 180° C. for 5 min. The stained chromatograms were then scanned with a Shimadzu CS-9000 spectrodensitometer in the reflectance mode at 400 nm.

Isolation of Phosphatidyl Choline From Amniotic Fluid

Aliquots of 0.1 mL of amniotic fluid obtained by amniocentesis at gestational ages ranging from 28 to 40 weeks were extracted with 0.6 mL of C-M (2:1, v/v) as indicated previously. Aliquots of 50 μL of the C-M extract (1:1, v/v) were applied as a streak to Whatman HP-K silica gel plates, the plates predeveloped in C-M (1:1, v/v) to 1 cm, and developed in one dimension using chloroform-ethanol-triethylamine-water (30:34:30:8, v/v/v/v) as the mobile phase. The band comigrating with phosphatidyl choline standard was scrapped, the silica gel extracted with 3 mL of C-M (2:1) and partitioned with 0.5 mL of distilled water. The corresponding emulsion was separated by centrifugation at 600 g for 5 min, the lower phase aspirated and evaporated to dryness. The purified phosphatidyl choline was then dissolved in 0.1 mL of D-PBS in a sonication bath, hydrolyzed with 0.1 mL of Bacillus cereus phospholipase C (160 U/mL) and the resulting diacylglycerols analyzed by HPTLC, as indicated previously.

Effect of Blood and Meconium Contamination on the Determination of DPPC

The effect of blood and/or meconium contamination on the determination of DPPC in amniotic fluid following hydrolysis of amniotic fluid with phospholipase C, was also evaluated. Blood and/or meconium, and/or urine (1 to 10% by volume) were added to 5 different amniotic fluid samples with DPPC concentrations ranging between 0.2 and 30 $\mu$g/mL and the concentration of DPPC determined as described previously. The concentration of DPPC as measured by free DPG was compared before and after addition of these contaminants.

Effect of Freezing and Thawing on the Determination of DPPC

The effect of freezing and thawing on the concentration of DPPC in amniotic fluid obtained following hydrolysis of amniotic fluid with phospholipase C, was investigated. Aliquots of freshly collected amniotic fluid (within 60 min of amniocentesis) and of the same frozen specimens, were analyzed by the procedure described herein and the results compared. Frozen specimens were subjected at least to three cycles of freeze/thaw.

Analysis of Fatty Acid Methyl Esters by Gas Chromatography

Aliquots of 0.1 mL of amniotic fluid, a solution of DPPC in D-PBS (10 $\mu$g/mL), and a solution of palmitoylpalmitoleoyl phosphatidylcholine (POPC) in D-PBS (10 $\mu$g/mL) were hydrolyzed separately with 0.1 mL of Bacillus cereus phospholipase C (160U/mL) and the lipids extracted with 1.2 mL of C-M (2:1, v/v), as indicated previously. The corresponding lipid residues were dissolved in 100 $\mu$L of C-M (1:1, v/v), applied to AgNO$_3$-HPTLC Whatman 5×5 cm HP-K silica gel microplates as a 4 cm streak, and developed in chloroform-acetone (95:5.5, v/v) to the top of the plate. Following development, the band comigrating with DPG and POG standards were scrapped from the plate, the silica gel extracted with 3 mL of C-M (2:1) and partitioned with 0.5 mL of distilled water. The corresponding emulsions were separated by centrifugation at 600 g for 5 min, the lower phases aspirated and evaporated to dryness. The lipid residues were hydrolyzed with 0.5 mL of 0.1M sodium methoxide at 40° C. for 1 h. After hydrolysis, the tubes were allowed to cool to room temperature, 1 mL of chloroform and 0.25 ml, of distilled water added, the emulsion centrifuged at 600 g for 5 min and the lower phases aspirated and evaporated to dryness. The resulting fatty acid methyl esters were dissolved in a volume of n-hexane to give concentrations of 1 $\mu$g/$\mu$L. The fatty acid methyl esters were analyzed by GC on a WCOT capillary column (Supelco-Wax-10, 30m×0.53 mm ID, 1.0 $\mu$m film) with initial and final temperatures in the column oven of 150° C. and 250° C., respectively, programmed to increase at a rate of 10° C./min. The analysis was performed on a Varian 3700 instrument equipped with flame ionization detector operated at a temperature of 260° C. Fatty acid methyl ester peaks were identified by comparison of retention times of standard mixtures and quantified using a Hewlett-Packard 3392A integrator, using methyl heptadecanoate as the internal standard. The identity of DPG and POG as the components comigrating with DPG and POG standards was based on the presence of methyl hexadecanoate (DPG) and methyl hexadecenoate and methylhexadecanoate (POG) as the fatty acid methyl esters identified in the gas chromatogram.

HPTLC-Autoradiographic Analysis

Aliquots of 10 $\mu$L of [$^{14}$C]-DPPC (30 $\mu$Ci/mL) solutions in D-PBS were spiked into term amniotic fluid samples, hydrolyzed with Bacilus Cereus phospholipase C and the resulting [$^{14}$C]-DPG extracted and redissolved in 4 $\mu$L of C-M (1: 1, v/v). Aliquots of 4 $\mu$L of the hydrolyzed [$^{14}$C]-DPPC extract and 0.3 $\mu$Ci of [$^{14}$C]-DPG were then applied to separate lanes of Whatman HP-K microplates and the diacylglycerides separated as indicated above. Following development, the plates were exposed to Kodak X-Omat film for 12 h at room temperature and the resulting bands scanned with a Shimadzu CS-9000 spectrodensitometer in the reflectance mode at 400 nm. Recoveries for DPG were calculated dividing the integration areas obtained for [$^{14}$C]-DPG by the amount of [$^{14}$C]-DPG recovered following enzymatic hydrolysis of [$^{14}$C]-DPPC with Bacilus Cereus phospholipase C.

Precision Analysis

Aliquots of 25 $\mu$L of 20 different amniotic fluid samples with DPPC values ranging from 0.2 to 30 $\mu$g/mL were analyzed in triplicate for the DPPC concentration following the procedure herein described. The standard deviation corresponding to the three values obtained was utilized to calculate the intraassay variation. Aliquots of 25 $\mu$L of a given amniotic fluid sample were also analyzed in triplicate for the DPPC concentration in 20 separate runs. The standard deviation corresponding to the 20 values of DPPC obtained was utilized to calculate the intraassay variation.

EXAMPLE 2

Accurate Prediction of Respiratory Distress Syndrome (RDS) Based on Quantitating the Concentration of Palmitoyl-Palmitoleoyl Phosphatidyl Choline (POPC) in Amniotic Fluid Palmitoyl-palmitoleoyl phosphatidylcholine (POPC) constitutes approximately 20% of the phosphatidylcholine molecular species of the mature fetal lung surfactant. POPC has been shown to accelerate adsorption of dipalmitoyl phosphatidylcholine (DPPC) and other surface-active material onto the alveolar air-liquid interphase. In this study, the neonatal respiratory status of 189 newborns delivered within 72 hours of amniocentesis was correlated to the concentration of POPC in amniotic fluid at the time of sampling using the DPPC test as described in Example 1.

Amniotic fluid samples were obtained from pregnancies with gestational ages ranging from 28 to 40 weeks. POPC concentration in amniotic fluid was determined in 25 $\mu$L aliquots of amniotic fluid by enzymatic hydrolysis with Bacillus cereus phospholipase C and micro-HPTLC reflectance spectrodensitometry. Twenty-nine samples contaminated with blood and/or meconium were excluded from the study. Of the 160 cases evaluated, 15 resulted in RDS. POPC values in those 15 RDS cases ranged between 0.25 and 1.61 $\mu$g/mL, with a mean value of 0.60±0.56 $\mu$g/mL. Of the 145 cases with mature lungs, 140 had POPC values that ranged between 2.5 and 12 µg/mL, with a mean value of 6.75±2.3 µg/mL; and 5 cases had POPC values below 2.5 µg/mL. Using a cut-off value of POPC above 2.5 µg/mL, determined from the population affected by RDS (mean+3 SD), the sensitivity and specificity of the test for RDS was 100% and 96%, respectively, while the positive and negative predictive values were 76% and 100%, respectively. POPC test turn-around time was 30 minutes. In conclusion, the concentration of POPC in amniotic fluid can be utilized as an accurate predictor of neonatal RDS.

EXAMPLE 3

Accurate Prediction of RDS in Complicated Pregnancies Based on Quantitation of Lung Lamellar Body Phosphoglycerides The neonatal respiratory status of 165 newborns delivered within 72 hours of amniocentesis was compared to the concentration of dipalmitoylphosphatidylcholine (DPPC) in amniotic fluid at the time of sampling. Amniotic fluid samples were obtained from pregnancies with gestational ages ranging from 27 to 40 weeks. One hundred and ten cases (67 percent) were delivered prior to 37 weeks. Indications for testing included cesarean section, premature rupture of membranes, and preterm labor. DPPC concentrations were determined in 25 µL aliquots of amniotic fluid by the DPPC test described in Example 1. Presence of blood or meconium to amniotic fluid did not significantly change the DPPC values.

Of the 165 cases evaluated, 20 resulted in RDS. DPPC concentrations in those 20 RDS cases ranged from 1 to 10 µg/mL with a mean value of 5.4±2.8 µg/mL. Of the 145 cases with mature lungs, only 2 had DPPC values below 12 µg/mL. When a DPPC cut-off value below 12 µg/mL was used, the sensitivity and specificity of the test for RDS were 100% and 99%, respectively. DPPC test turn-around time was 30 minutes.

The study demonstrates that the DPPC test constitutes an accurate predictor of RDS in complicated pregnancies, particularly those remote from term. This valuable information could significantly improve the management of these pregnancies.

EXAMPLE 4

Comparison with the Abbott-TDx Test

The neonatal respiratory status of 160 newborns delivered within 72 hours of amniocentesis was compared to the concentration of DPPC in amniotic fluid and fluorescence polarization (Abbott-TDx test). Amniotic fluid samples were obtained from pregnancies with gestational ages ranging from 27 to 40 weeks. Indications for testing included cesarean section, PROM, and preterm labor. Sixty six percent of the babies delivered had gestational ages between 31 and 36 weeks. A TDx test result<70 was used to predict RDS and a TDx test result>70 to predict fetal lung maturity. A DPPC test result<12 µg/mL was used to predict RDS and a test result>12 µg/mL to predict fetal lung maturity. Of the 160 cases evaluated, 15 resulted in RDS. Of the 15 RDS cases, 12 had TDx scores<70 and 3>70. All 15 RDS cases were correctly predicted with DPPC values <12 µg/mL. Of the 145 cases with mature lungs, 74 had TDx scores<70 and only 2 had DPPC values<12 µg/mL. The sensitivity and specificity of the TDx test for RDS were 80% and 49%, respectively. The positive and negative predictive values of the TDx test were 14% and 96%, respectively. The sensitivity and specificity for DPPC test were 100% and 99% and the positive and negative predictive values were 91% and 100%, respectively.

The outcome of 101 discordant cases with immature TDx and mature DPPC is shown in the table below. Patients in the non-delayed group were delivered within 48 hours of testing, while those in the delayed group were delivered at a mean of 17 days after testing.

| GROUP | M-LOS (days) | EGA (weeks) | NICU-LOS (days) | RDS cases |
|---|---|---|---|---|
| non-delayed N = 72 | 1.0 ± 1.1** | <33 (26) | 8.2 ± 2.3 | 0 |
|  |  | ≧33 (46) | 2.5 ± 2.1* | 0 |
| delayed N = 39 | 7.6 ± 6.8** | <33 (14) | 8.8 ± 3.1 | 0 |
|  |  | ≧33 (25) | 2.6 ± 2.4* | 0 |

**(p < 0.05); *(p > 0.10)

M-LOS: maternal length of stay; NICU-LOS: NICU length of stay; EGA: estimated gestational age at delivery.

In this study, premature infants with immature TDx values, but mature DPPC concentrations did not develop RDS. This study demonstrates that the DPPC test is a more accurate predictor of RDS in complicated pregnancies than fluorescence polarization. The use of the DPPC test in preterm pregnancies may allow for safe delivery, thereby avoiding unnecessary use of tocolytics, prolonged hospitalization, and potential maternal and fetal risks.

EXAMPLE 5

Analysis of Dipalmitoyl Phosphatidylcholine (DPPC) by Infrared Spectroscopy

Figure 7:
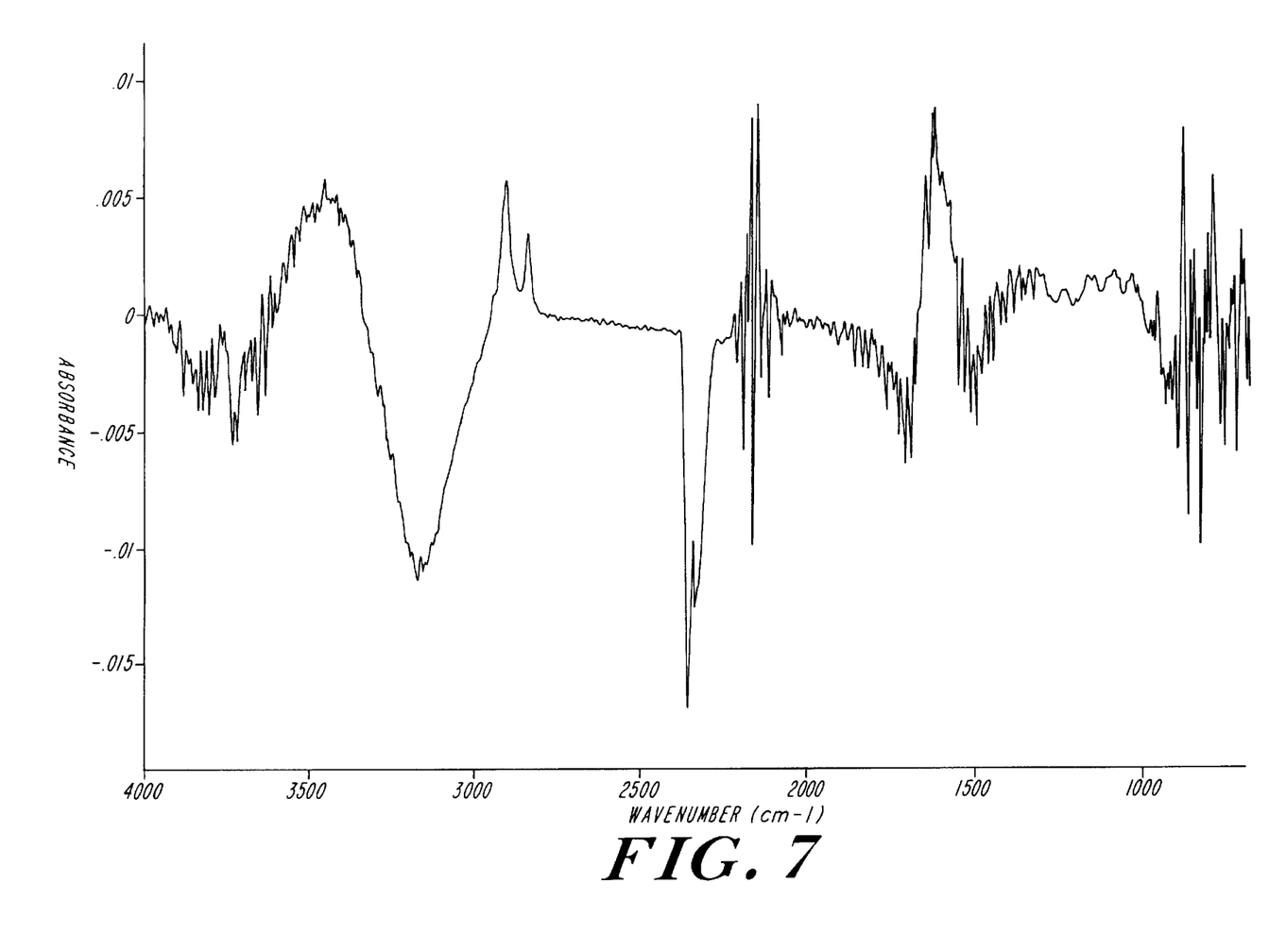
FIG. 7: A spectrum obtained based on 32 scans at a rate of 4 scans/sec on mature amniotic fluid using a Bio-Rad-Win Ft-IR infrared spectrometer.
Figure 8:
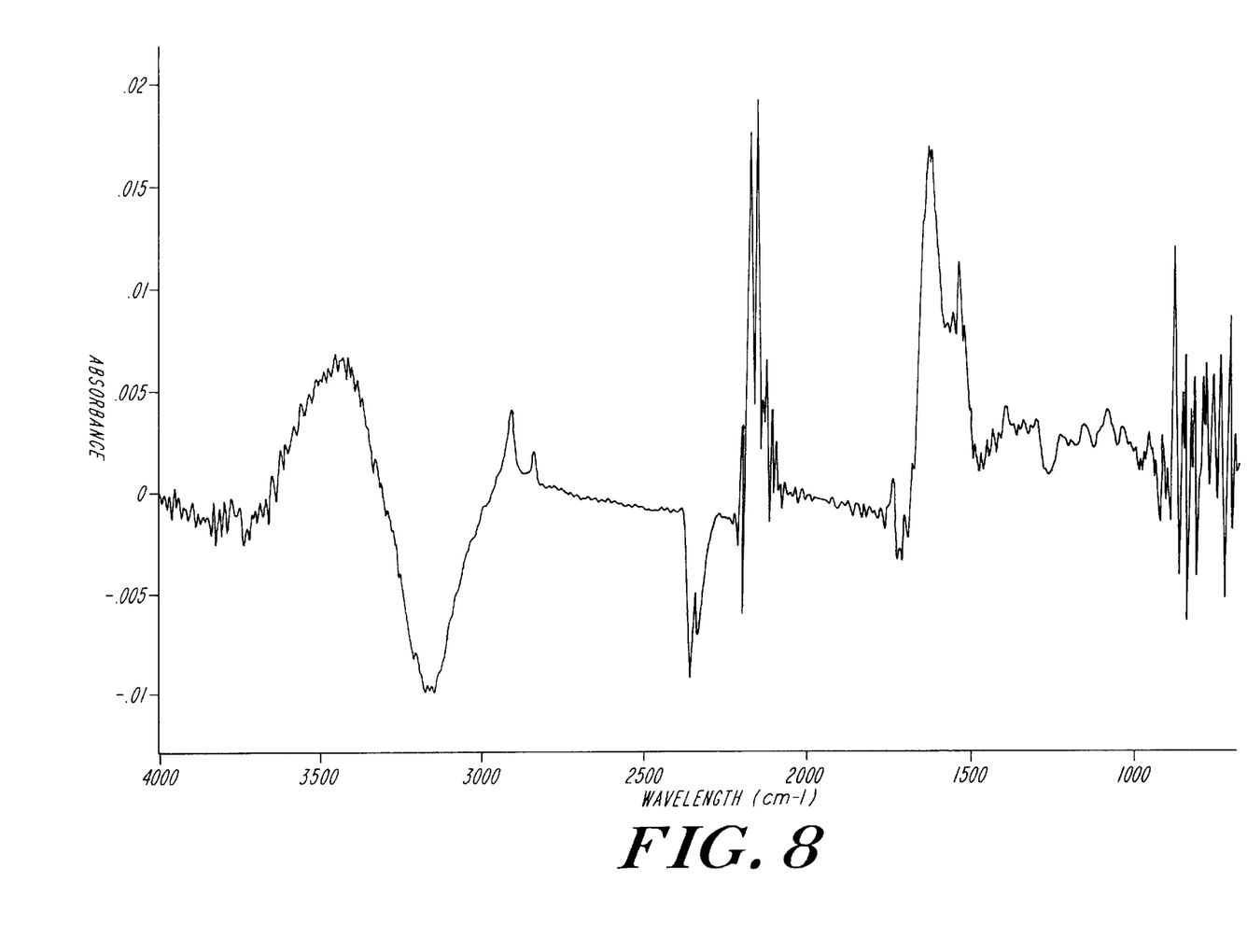
FIG. 8: A spectrum obtained based on 32 scans at a rate of 4 scans/sec on amniotic fluid obtained from a pregnancy where the newborn developed RDS using a Bio-Rad-Win Ft-IR infrared spectrometer.
Figure 9:
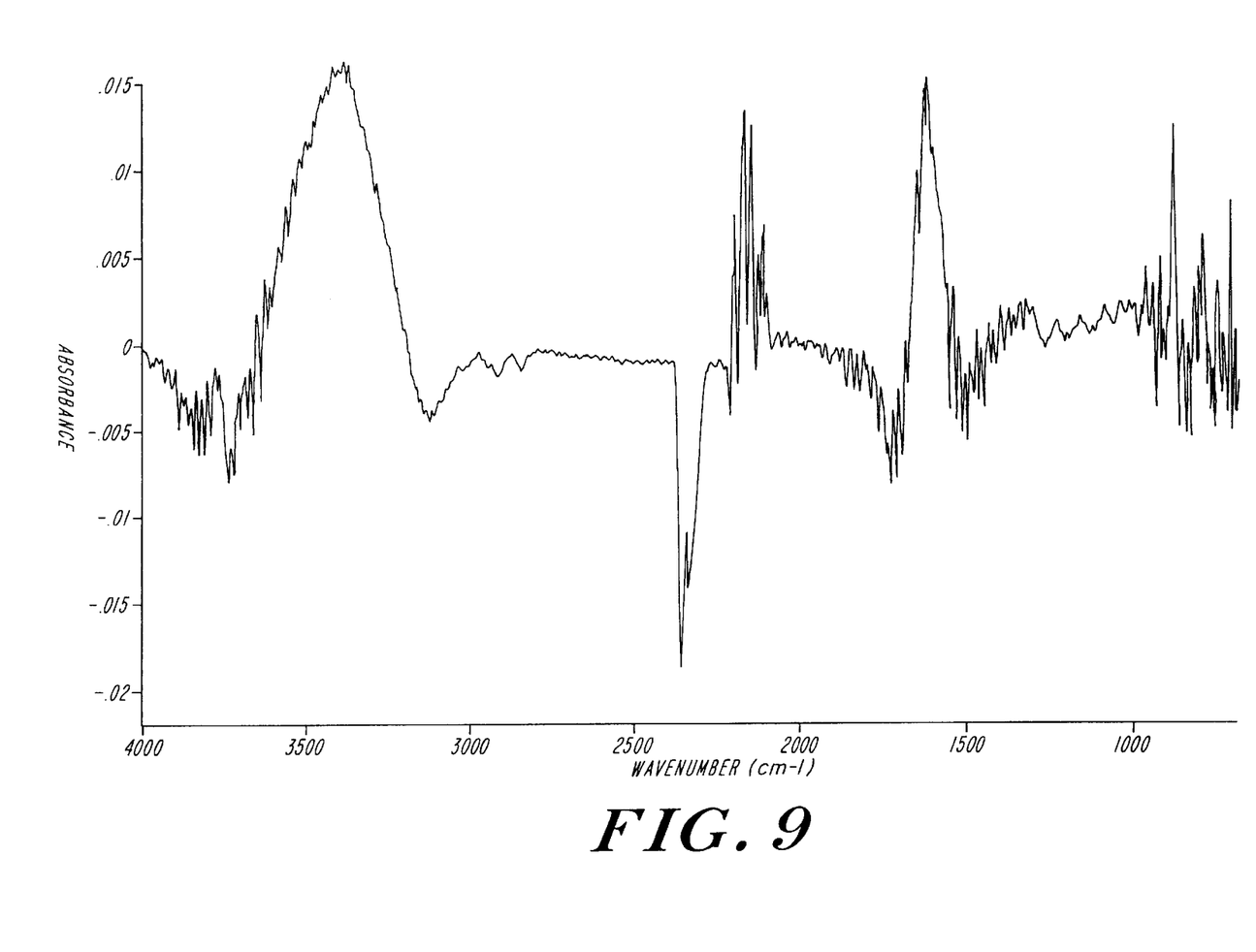
FIG. 9: A spectrum obtained based on 32 scans at a rate of 4 scans/sec on borderline amniotic fluid using a Bio-Rad-Win Ft-IR infrared spectrometer.
Figure 10:
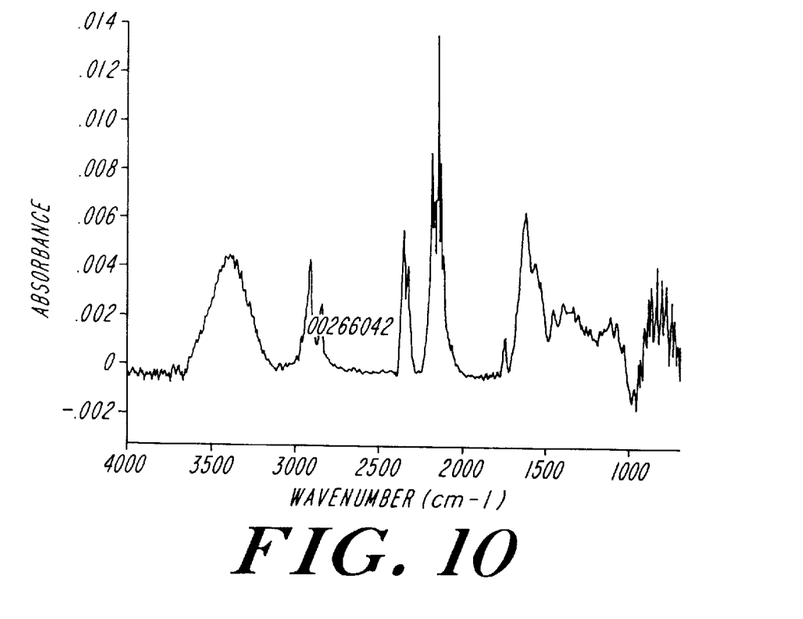
FIG. 10: A spectrum obtained based on 1024 scans at a rate of 4 scans/sec on mature amniotic fluid using a Bio-Rad-Win Ft-IR infrared spectrometer.

A fiber optic probe is inserted into a test tube containing ≧0.5mL of amniotic fluid and the absorption corresponding to the stretching frequencies of the phospholipid groups R—C=C—H—C—H—C=C—R' ($2965\ cm^{-1}$), R—H—C—H—R' ($2913\ cm^{-1}$), R—C=O—R' ($1750\ cm^{-1}$), and R—P=O—R' ($1150\ cm^{-1}$) obtained by infrared spectroscopy using a Bio-Rad-Win FT-IR spectrometer. A total of 32 scans at a rate of 4 scans/sec were obtained for the samples shown in FIGS. 7–10. A typical spectrum of a mature amniotic fluid is shown in FIG. 7. FIG. 8 corresponds to an amniotic fluid obtained from a pregnancy where the newborn developed RDS. FIG. 9 corresponds to a borderline amniotic fluid. FIG. 10 corresponds to the sample used in FIG. 7 after the accumulation of 1024 scans.

EXAMPLE 6

Analysis of DPG by Infrared Spectroscopy

Aliquots of 0.5 mL of an amniotic fluid sample are treated with 50 µL of *Bacillus cereus* phospholipase C in D-PBS (1600 U/mL) and incubated at 37° C. for 5 min. A fiber optic probe is then inserted into the amniotic fluid sample contained in a test tube and the absorption corresponding to the stretching frequencies of the diglyceride groups R—C=C—H—C—H—C=C—R' ($2965\ cm^{-1}$), R—H—C—H—R' ($2913\ cm^{-1}$), and R—C=O—R' ($1750\ cm^{-1}$) obtained by infrared spectroscopy using a Bio-Rad-Win FT-IR spectrometer.

EXAMPLE 7

Analysis of DPG by Gas Chromatography

Aliquots of 25 µL of an amniotic fluid sample are treated with 25µL of *Bacillus cereus* phospholipase C in D-PBS (160 U/mL), incubated at 37° C. for 5 min, extracted with 6 volumes of chloroform-methanol (2:1, v/v), centrifuged at 600 g for 3 min, and the lower phase aspirated and evaporated to dryness. The lipid residue is then dissolved in 10 µL of chloroform-methanol 2:1 and a 1 µL aliquot injected in a Shimadzu GC-6AM Gas Chromatograph provided with an FID detector. The column is a Supelco GP 5% DEGS-PS 100/120 Supelcoport 3×2mm (Supelco, Bellefonte, Pa.). Nitrogen flow rate is 22 mL/min. Column temperature is kept constant at 200° C. Injector and FID detector temperature are 300° C. DPPC eluted with a retention time of 2 minutes and can be resolved from other diglyceride species including palmitoyl-palmitoleoyl-glycerol, palmitoyl-oleoyl-glycerol, dimyristoyl glycerol, and distearoyl glycerol.

EXAMPLE 8

Analysis of DPG by High Pressure Liquid Chromatography (HPLC)

Aliquots of 25 µL of amniotic fluid are treated with 25 µL of *Bacillus cereus* phospholipase C in D-PBS (160 U/mL), incubated at 37° C. for 5 min, extracted with 6 volumes of chloroform-methanol (2:1, v/v), centrifuged at 600 g for 3 min and the lower phase aspirated and evaporated to dryness. The lipid residue is then dissolved in 10 µL of chloroform-methanol 2:1 and a 5 µL aliquot injected into a Waters HPLC instrument using a $AgNO_3$-impregnated silica gel column (CromSpher Lipid HPLC column from Chrompack Inc., Raritan, N.J.) and a variety of mobile phases, including chloroform-acetone 95:5 (v/v) used for separation. Diacylglycerol peaks are detected in the UV mode at 210 nm.

EXAMPLE 9

Analysis of DPG in Amniotic Fluid by Fluorescence Polarization

Aliquots of 0.5 mL of amniotic fluid are treated with 50 µL of *Bacillus cereus* phospholipase C in D-PBS (1600 U/mL) and incubated at 37° C. for 5 min. Following incubation, DPG-BODIPY fluorescence derivative (Molecular Probes Inc., Eugene, Oreg.) is added to the amniotic fluid sample, the mixture equilibrated for 5 min at room temperature, and the level of fluorescence polarization determined.

EXAMPLE 10

Analysis of DPPC in Amniotic Fluid by $^1$H-NMR

Aliquots of 0.5 mL of the amniotic fluid is extracted with 6 volumes of chloroform-methanol (2:1 v/v), the lower phase aspirated, evaporated to dryness, dissolved in 0.5 mL of deuterated chloroform and transferred to a 200×5 mm NMR tube (Wilmad Glass Co., Buena, N.J.). Proton NMR spectra are obtained on a Bruker AM-500 (555 MHz) spectrometer equipped with an Aspect 3000 computer, operating in the Fourier-transform mode with quadrature detection. Integrated one-dimensional spectra are obtained in the range of 5 KHz (0 to 10 ppm) and 16,000 sampling points. Methylene chain protons (R—H—C—H—R') are observed at 1.2 ppm. Allylic (R—C=C—H—C—R') and bis-allylic (R—C=C—H—C—H—C=C—R') methylene protons are observed at 5.2 and 5.6 ppm, respectively. Resonances at 1.5, 2.25 and 5.01 ppm correspond to β-protons (R—H—C—C—H—C=O—R') to the carbonyl ester, α-protons to the carbonyl ester (R—H—C—C—H—C=O—R'), and glycerol methine proton (R—$CH_2$—R'—C—H—$CH_2$—R'), respectively. The presence of these resonances in an amniotic fluid sample or other biological samples can be used for the analysis of DPPC.

EXAMPLE 11

Analysis of DPG by Immunoreaction

Monoclonal and polyclonal antibodies against DPG can be obtained from mouse hybridomas or by animal immunization, following conjugation of DPG with a protein hapten. Aliquots of 0.5 mL of amniotic fluid are treated with 50 µL of *Bacillus cereus* phospholipase C (1600 U/mL) and incubated for 5 minutes at 37° C. Following incubation, the sample is transferred to a test tube containing peroxidase or alkaline phosphatase-labeled anti-DPG polyclonal antibodies dissolved in an isotonic buffer and incubated at room temperature for 10 minutes (tube #1). Then a test strip with bound unlabeled anti-DPG antibodies is dipped into tube #1 and incubated at room temperature for 15 minutes. The test strip is then dipped in tube #2 containing the enzyme substrate solution, incubated at room temperature for 15 minutes, and the development of color in the test strip monitored for a period of 30 seconds. Application of this test kit for the monitoring of fetal lung maturity will involve a built-in calibration system where the appearance of color in the test strip will correspond to a DPG value in amniotic fluid sample $\leq 12$ µg/mL. Should polyclonal antibodies against DPG cross-react with diglyceride species other than DPPC and POPC, the results obtained should not be significantly affected by the presence of the interfering molecular species, since 90% of the molecular species of PC in amniotic fluid correspond to the combined DPPC and POPC species.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A process for detecting or quantitating a phosphoglyceride of interest in a sample containing the phosphoglyceride of interest and other phosphoglycerides, comprising the steps of:

a) performing a phosphoglyceride specific hydrolysis on the sample, thereby yielding diglycerides from the phosphoglyceride of interest and the other phosphoglycerides; and b) detecting or quantitating the diglyceride corresponding to the phosphoglyceride of interest, as an indication of the presence or quantity of the phosphoglyceride of interest in the sample.

2. A process of claim 1, wherein the sample is a biological fluid.

3. A process of claim 2, wherein the biological fluid is selected from the group consisting of: amniotic fluid, maternal cervical secretions, lung lavage, plasma, spinal fluid and urine.

4. A process of claim 1, wherein the phosphoglyceride specific hydrolysis is accomplished by contacting the sample with a phospholipase enzyme at an appropriate temperature and for an appropriate period of time for complete hydrolysis of the phosphoglyceride of interest and the other phosphoglycerides.

5. A process of claim 4, wherein the phospholipase is selected from the group consisting of: phospholipase C, phospholipase D, phospholipase $A_1$ and phospholipase $A_2$.

6. A process of claim 5, wherein the phospholipase is phospholipase C from *Bacillus cereus* or *Clostridium perfinges*.

7. A process of claim 1, wherein prior to step b), the digylycerides produced in step a) are extracted from the sample by adding an organic solvent to the sample.

8. A process of claim 7, wherein the organic solvent is selected from the group consisting of: chloroform-methanol, ethyl acetate, hexane-isopropanol and hexane.

9. A process of claim 7, wherein subsequent to addition of the organic solvent and prior to step b), less polar compounds generated by phosphoglyceride specific hydrolysis are resolved from one another in a resolution step.

10. A process of claim 9, wherein the resolution step is selected from the group consisting of a high resolution chromatography and a capillary electrophoresis.

11. A process of claim 10, wherein the resolution step is a high resolution chromatography selected from the group consisting of: a liquid, column chromatography, gas column chromatography (GC); and a planar, liquid chromatography.

12. A process of claim 11, wherein the high resolution chromatography is liquid, column chromatography selected from the group consisting of: high performance liquid chromatography (HPLC), ion exchange chromatography, and gel chromatography.

13. A process of claim 11, wherein the high resolution chromatography is planar, liquid chromatography selected from the group consisting of: thin layer chromatography (TLC) and high performance TLC (HPTLC).

14. A process of claim 13, wherein the planar, liquid chromatography is HPTLC using high performance silica gel layers mass modified with cations.

15. A process of claim 14, wherein the cations are selected from the group consisting of silver nitrate ($AgNO_3$) and boric acid ($BH_4$).

16. A process for assessing lung maturity of a fetus in a pregnant woman prior to labor, comprising the steps of:
   a) obtaining from a pregnant woman an amniotic fluid sample, which contains a phosphoglyceride present in mature lungs and other phosphoglycerides,
   b) performing a phosphoglyceride specific hydrolysis on the amniotic fluid sample, thereby yielding diglycerides from the phosphoglyceride present in mature lungs and the other phosphoglycerides; and
   c) quantitating the diglyceride that corresponds to the phosphoglyceride present in mature lungs and comparing the value obtained to a standard value to assess the lung maturity of the fetus.

17. A process of claim 16, wherein the diglyceride from the phosphoglyceride present in mature lungs is dipalmitoyl glycerol (DPG).

18. A process of claim 16, wherein the phosphoglyceride specific hydrolysis is accomplished by contacting the sample with a phospholipase enzyme at an appropriate temperature and for an appropriate period of time for complete hydrolysis of the phosphoglycerides.

19. A process of claim 18, wherein the phospholipase is selected from the group consisting of: phospholipase C, phospholipase D, phospholipase $A_1$ and phospholipase $A_2$.

20. A process of claim 19, wherein the phospholipase is phospholipase from *Bacillus cereus* or *Clostridium perfinges*.

21. A process of claim 16, wherein prior to step b), the diglycerides produced in step a) are extracted from the sample by adding an organic solvent to the sample.

22. A process of claim 21, wherein the organic solvent is selected from the group consisting of chloroform-methanol, ethyl acetate, hexane-isopropanol and hexane.

23. A process of claim 21 wherein subsequent to addition of the organic solvent and prior to step b) the diglycerides generated by phosphoglyceride specific hydrolysis are resolved from one another in a resolution step.

24. A process of claim 23, wherein the resolution step is selected from the group consisting of a high resolution chromatography and a capillary electrophoresis.

25. A process of claim 24, wherein the resolution step is high resolution chromatography selected from the group consisting of: a liquid, column chromatography, gas column chromatography (GC); and a planar, liquid chromatography.

26. A process of claim 25, wherein the high resolution chromatography is liquid, column chromatography selected from the group consisting of: high performance liquid chromatography (HPLC), ion exchange chromatography, and gel chromatography.

27. A process of claim 25, wherein the high resolution chromatography is planar, liquid chromatography selected from the group consisting of: thin layer chromatography (TLC) and high performance TLC (HPTLC).

28. A process of claim 27, wherein the planar, liquid chromatography is HPTLC using high performance silica gel layers mass modified with cations.

29. A process of claim 28, wherein the cations are selected from the group consisting of silver nitrate ($AgNO_3$) and boric acid ($BH_4$).

30. A process for assessing the condition of a subject's lungs, comprising the steps of:
   a) obtaining from a subject a biological sample which contains a phosphoglyceride present in healthy lungs and other phosphoglycerides;
   b performing a phosphoglyceride specific hydrolysis on the biological sample, thereby yielding diglycerides from the phosphoglyceride present in healthy lungs and the other phosphoglycerides; and
   c quantitating the diglyceride that corresponds to the phosphoglyceride present in healthy lungs and comparing the value obtained to a standard value to assess the relative health of the subject's lungs.

31. A process of claim 30, wherein the biological sample is selected from the group consisting of: lung lavage, plasma, spinal fluid, or urine.

* * * * *

UNITED STATES PATENT AND TRADEMARK OFFICE
CERTIFICATE OF CORRECTION

PATENT NO. : 5,856,196
DATED : January 5, 1999
INVENTOR(S) : Juan G. Alvarez and Jack Ludmir It is certified that error appears in the above-identified patent and that said Letters Patent is hereby corrected as shown below:

On the title page, [*] Notice, please replace "Pat. No. 5,443,909" with -- Pat. No. 5,443,989--

Signed and Sealed this

Thirteenth Day of July, 1999

Attest:

Q. TODD DICKINSON

*Attesting Officer*    *Acting Commissioner of Patents and Trademarks*